(12) United States Patent
Wager et al.

(10) Patent No.: US 10,342,821 B2
(45) Date of Patent: Jul. 9, 2019

(54) SYSTEMS AND METHODS TO IMPROVE ORGAN OR TISSUE FUNCTION AND ORGAN OR TISSUE TRANSPLANT LONGEVITY

(71) Applicant: PROTERRIS, INC., Boston, MA (US)

(72) Inventors: Jeffrey D. Wager, Boston, MA (US); Joseph Wager, Boston, MA (US); Alex Stenzler, Garden Grove, CA (US); David Pinsky, Ann Arbor, MI (US); Augustine Choi, Boston, MA (US)

(73) Assignee: PROTERRIS, INC., Boston, MA (US)

( * ) Notice: Subject to any disclaimer, the term of this patent is extended or adjusted under 35 U.S.C. 154(b) by 101 days.

(21) Appl. No.: 15/702,091

(22) Filed: Sep. 12, 2017

(65) Prior Publication Data

US 2018/0000859 A1    Jan. 4, 2018

Related U.S. Application Data

(63) Continuation of application No. 14/687,740, filed on Apr. 15, 2015, now Pat. No. 9,789,133.

(60) Provisional application No. 61/979,712, filed on Apr. 15, 2014, provisional application No. 61/993,140, filed on May 14, 2014.

(51) Int. Cl.
| | |
|---|---|
| *A61K 33/04* | (2006.01) |
| *A61K 33/00* | (2006.01) |
| *G01N 33/72* | (2006.01) |
| *A61M 16/00* | (2006.01) |
| *A61M 16/10* | (2006.01) |
| *A61M 16/12* | (2006.01) |

(52) U.S. Cl.
CPC ......... *A61K 33/00* (2013.01); *A61M 16/0051* (2013.01); *A61M 16/026* (2017.08); *A61M 16/10* (2013.01); *A61M 16/12* (2013.01); *G01N 33/721* (2013.01); *A61M 2016/1035* (2013.01); *A61M 2202/0208* (2013.01); *A61M 2202/0233* (2013.01); *G01N 2333/805* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,542,858 | B1 | 4/2003 | Grass et al. |
| 6,581,599 | B1 | 6/2003 | Stenzler |
| 6,955,171 | B1 | 10/2005 | Figley et al. |
| 7,238,469 | B2 | 7/2007 | Bach et al. |
| 7,364,757 | B2 | 4/2008 | Otterbein et al. |
| 7,523,752 | B2 | 4/2009 | Montgomery et al. |
| 7,574,246 | B2 | 8/2009 | Krebs et al. |
| 7,678,390 | B2 | 3/2010 | Choi et al. |
| 7,687,079 | B2 | 3/2010 | Otterbein et al. |
| 7,691,416 | B2 | 4/2010 | Otterbein et al. |
| 7,945,301 | B2 | 5/2011 | Krebs et al. |
| 7,981,448 | B2 | 7/2011 | Otterbein et al. |
| 8,091,549 | B2 | 1/2012 | Montgomery et al. |
| 8,128,963 | B2 | 3/2012 | Pinsky et al. |
| 8,397,721 | B2 | 3/2013 | Montgomery et al. |
| 8,517,015 | B2 | 8/2013 | Montgomery et al. |
| 8,607,791 | B2 | 12/2013 | Milne et al. |
| 8,616,204 | B2 | 12/2013 | Montgomery et al. |
| 8,720,440 | B2 | 5/2014 | Montgomery et al. |
| 8,778,413 | B2 | 7/2014 | Usansky et al. |
| 8,893,717 | B2 | 11/2014 | Montgomery et al. |
| 2006/0081244 | A1 | 4/2006 | Bouillon et al. |
| 2007/0062527 | A1 | 3/2007 | Montgomery et al. |
| 2012/0180790 | A1 | 7/2012 | Montgomery et al. |
| 2014/0287066 | A1 | 9/2014 | Usansky et al. |

FOREIGN PATENT DOCUMENTS

| | | |
|---|---|---|
| WO | 2003096977 | 11/2003 |
| WO | 2013022946 | 2/2013 |
| WO | 2013148232 | 10/2013 |
| WO | 2015073912 | 5/2015 |

OTHER PUBLICATIONS

EPA, "Ar Quality Criteria for Carbon Monoxide," Chapter 5, Pharmacokinetics and Mechanisms of Action of Carbon Monoxide, pp. 5-1-5-30, Jun. 2000.
International Search Report, International Appln. No. PCT/US2014/065822, dated Feb. 11, 2015, 2 pages.
International Search Report, International Appln. No. PCT/US2015/026006, dated Jul. 2, 2015, 3 pages.
Mahoney, A.M., "Noninvasive Measurement of Carboxyhemoglogin Levels for Adjustment of Diffusion Capacity Measured During Pulmonary Function Testing," Respiratory Care, 2007, vol. 52, No. 12 pp. 1740-1743.

*Primary Examiner* — Susan T Tran
(74) *Attorney, Agent, or Firm* — Morgan, Lewis & Bockius LLP

(57) ABSTRACT

The present invention provides for systems and methods for inhaled CO therapy to prevent, attenuate, or delay processes that accelerate the loss of organ or tissue function, thereby increasing the lifespan of transplanted organs or tissues, or slowing the decline of native organs or tissues, or delaying the need for replacement of diseased native organs with organ transplants. Such biological processes that are prevented, attenuated, or delayed include chronic persistent inflammation, fibrosis, scarring, as well as immunologic or autoimmune attack.

20 Claims, 4 Drawing Sheets

SYSTEMS AND METHODS TO IMPROVE ORGAN OR TISSUE FUNCTION AND ORGAN OR TISSUE TRANSPLANT LONGEVITY

PRIORITY

This application claims priority to U.S. Provisional Application No. 61/979,712 filed Apr. 15, 2014, and U.S. Provisional Application No. 61/993,140 filed May 14, 2014, the entire contents of which are hereby incorporated by reference in their entireties.

FIELD OF THE INVENTION

In the various aspects, the invention provides systems and methods for improving organ and tissue function, and for preventing, attenuating, or delaying loss of organ or tissue function, including for transplanted and native organs/tissues. The systems and methods of the invention are based on the delivery of therapeutic regimens of inhaled carbon monoxide (CO).

BACKGROUND

Chronic failure of organs and tissues often involves replacement of highly differentiated cells with scarring connective tissue. For example, chronic renal disease is characterized by progressive decline of renal function with continuous accumulation of extracellular matrix, resulting in diffuse fibrosis. Chronic failure of transplanted organs may likewise be associated with progressive scarring, in addition to immunological rejection that further impair the long term survival of the graft.

Methods and systems for preventing, delaying, or attenuating loss of organ or tissue function, including for both native and transplanted organs and tissues, are needed. In particular, methods and systems are needed to prevent, attenuate, or delay chronic persistent inflammation, fibrosis, scarring, and immunological attack, among other biological processes.

SUMMARY OF THE INVENTION

The present invention in various aspects and embodiments provides methods and systems for inhaled carbon monoxide (CO) therapy to improve organ or tissue function and longevity, including for transplanted organs and tissues as well as declining or diseased native organs/tissues.

In various aspects, administration of an inhaled CO regimen according to the invention prevents, attenuates, or delays processes that accelerate the loss of organ or tissue function, thereby increasing the lifespan of transplanted organs/tissues, or slowing the decline of native organs/tissues, or delaying the need for replacement of diseased native organs or tissue with transplants. Such biological processes that are prevented, attenuated, or delayed include chronic persistent inflammation, fibrosis, scarring, as well as immunologic or autoimmune attack.

In certain embodiments, the invention provides inhaled CO therapy to reduce the incidence or reduce the likelihood of organ transplantation failure, including preventing, attenuating, or treating acute rejection, chronic allograft rejection, vascular rejection, graft versus host disease, and/or delayed graft function (DGF) after kidney transplantation. In various embodiments, the invention provides for increased transplantation success with types of organ donations that have been statistically less successful in terms of long term graft survival or avoiding DGF, thereby increasing the availability of acceptable donor organs. In various embodiments, the invention prevents, attenuates, or delays immunologic rejection of transplanted organs or tissues, fibrosis or fibrotic scarring of transplanted organs or tissues, compromised blood supply to transplanted organs/tissues, or persistent or chronic inflammation leading to the destruction and impairment of transplanted organs or tissues. In some embodiments, the invention allows reduction or elimination of immunosuppressive therapy, for example, following allograft transplantation.

In the various embodiments, CO is administered one or more of pre-operatively, intra-operatively, or post-operatively to an organ or tissue transplant patient. CO therapy may be provided during the peri-operative period, as well substantially before or substantially after the peri-operative period.

In certain embodiments, the invention provides methods for preventing, delaying, or treating fibrotic conditions of organs or tissues such as the kidney, lung, heart, liver, pancreas, gastrointestinal tract, and skin. Exemplary conditions include chronic kidney fibrosing conditions, chronic hepatic fibrosing conditions (e.g., non-alcoholic steatohepatitis, or NASH), chronic lung fibrosing conditions (e.g., idiopathic pulmonary fibrosis or IPF), myocardial fibrosis, esophageal fibrosis, vascular fibrosis, and systemic diseases marked by dysregulated injury repair and/or systemic fibrosis, including progressive systemic sclerosis (PSS) or scleroderma.

In still other aspects, the invention provides systems and methods for safely delivering therapeutic levels of inhaled CO to a patient, with such systems and methods being suitable for acute and chronic (e.g., prolonged) treatment. For example, the invention provides systems and methods for accurately delivering inhaled CO within its therapeutic window, thereby rendering inhaled CO suitable for managing chronic conditions over a prolonged period of time.

In some embodiments, the invention provides for methods and systems for delivering inhaled CO to a patient at a constant alveolar concentration that maintains a selected or desired CO level in the patient for a desired period of time. These systems and methods provide for therapeutic advantages in CO delivery for a variety of chronic conditions. In some embodiments, the CO dose is controlled by measuring inhaled CO uptake by the patient at a select CO dose for a select period of time. The measurement of CO uptake allows for close approximation of diffusivity of the patient's lungs for CO ($DL_{CO}$), which in turn allows personalized correlation between CO dose, exposure time, and blood CO level. Thus, CO level in a patient can be carefully controlled to rapidly achieve the desired CO target, and then maintain that target for a desired duration. Various measurements can be used as a proxy for CO level, including carboxy-hemoglobin concentration in blood, among others.

For example, systems of the invention can comprise: a source of gas comprising carbon monoxide, a gas metering device operably connected to the CO source, a gas mixing device for preparing a gas having a desired CO concentration for delivery, a CO gas delivery unit, and a computer system programmed to perform calculations based on relationships defined by the Coburn-Foster-Kane equation (CFK equation). For example, using the relationships defined by the CFK equation, the system calculates $DL_{CO}$ for the patient based on CO uptake (e.g., CO-Hb input values, which include a baseline CO-Hb level, and a level measured at a selected time point during CO administration). In some embodiments, the computer system controls the dose of CO delivered to a patient, based on the determined $DL_{CO}$ and a desired CO endpoint and duration to reach the endpoint, as well as duration to maintain the CO endpoint. In some embodiments, the system controls the CO concentration of the inspired gas and duration, for at least two different doses of CO.

The frequency of administration of inhaled CO in accordance with these aspects can be, for example, between once monthly to a plurality of times per day, to prevent, arrest, delay, or attenuate the progression of chronic processes that lead to impaired function of transplanted or native organs or tissues.

Other aspects and embodiments of the invention will be apparent from the following detailed description.

DESCRIPTION OF INVENTION

Figure 1:
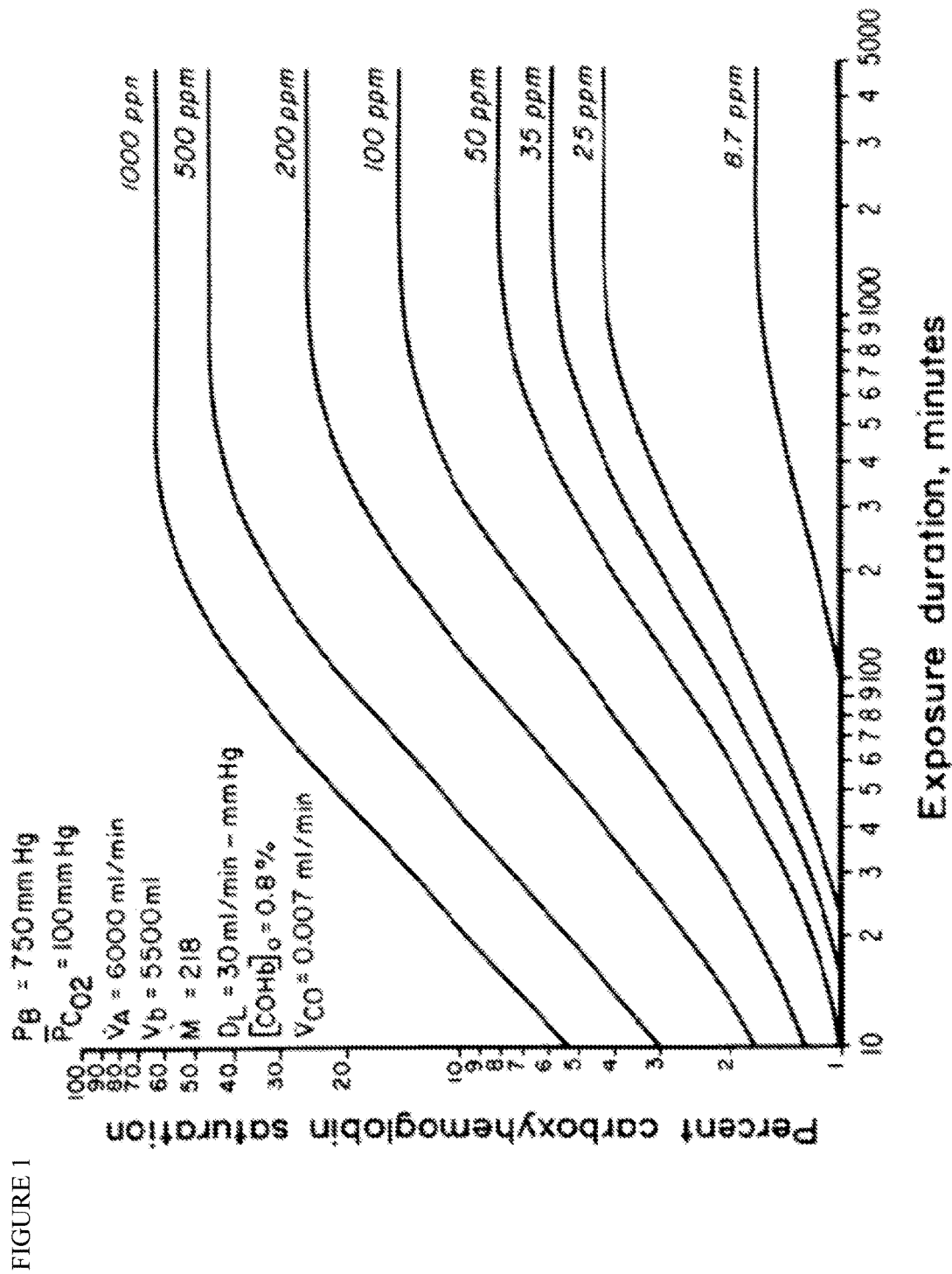
FIG. 1 shows exemplary curves for percent carboxyhemoglobin saturation as a function of CO exposure duration at various CO concentration levels from 8.7 ppm to 1000 ppm. Other variables of the CFK equation are provided. From, Peterson J E, et al., *Predicting the carboxyhemoglobin levels resulting from carbon monoxide exposures, J Applied Physiol* Vol. 39(4):633-638 (1975).

The present invention in various aspects and embodiments provides carbon monoxide therapy to improve organ or tissue function and longevity, including for transplant organs and tissues as well as diseased or declining native organs. For example, administration of a CO regimen as described herein can prevent, attenuate, or delay processes that accelerate the loss of organ or tissue function, thereby increasing the lifespan of transplants, as well as delaying the need for replacement of diseased native organs/tissue with transplants. Such biological processes that are prevented, attenuated, or delayed include those involved in immunologic rejection of transplanted organs or tissues, fibrosis or fibrotic scarring of transplanted or native organs or tissues, compromised blood supply to transplanted or native organs or tissues, or persistent or chronic inflammation leading to the destruction and impairment of transplanted or native organs and tissues.

In some embodiments, the patient has a condition characterized by fibrosis. Fibrosis is the formation of excess fibrous connective tissue in an organ or tissue in a reparative or reactive process. In response to injury this is referred to as scarring. Fibrosis can obliterate the architecture and function of an organ or tissue. Fibrosis can be associated with a generalized inflammatory state, with increased circulating inflammatory mediators. For example, in some embodiments, the patient has a condition selected from a chronic kidney fibrosing condition, a chronic hepatic fibrosing condition (e.g., non-alcoholic steatohepatitis, or NASH), a chronic lung fibrosing condition (e.g., idiopathic pulmonary fibrosis or IPF), myocardial fibrosis, pancreatic fibrosis, pancreatitis, gastrointestinal fibrosis, vascular fibrosis or strictures, or other systemic disease marked by dysregulated injury repair and/or systemic fibrosis, including progressive systemic sclerosis (PSS) or scleroderma. Additional conditions include cirrhosis, atrial fibrosis, esophageal fibrosis, esophageal or gastrointestinal strictures, Crohn's Disease, Inflammatory Bowel Disease, toxic megacolon, paralytic ileus, arthrofibrosis, arthritis, and nephrogenic systemic fibrosis. Target organs and tissues include kidney, lung, heart, liver, gastrointestinal tract, pancreas, bone marrow, and skin.

In some embodiments, the patient has an acute or chronic inflammatory, hyperproliferative, or fibrotic condition of the lungs, as disclosed in PCT/US2014/065822, which is hereby incorporated by reference in its entirety. Such conditions include pulmonary fibrosis (including Idiopathic Pulmonary Fibrosis, or IPF), asthma, emphysema, Chronic Obstructive Pulmonary Disease (COPD), pulmonary arterial hypertension (PAH), cystic fibrosis (CF), Acute Respiratory Distress Syndrome (ARDS), bronchiectasis, Ventilator-Assisted Pneumonia (VA), and lung transplantation.

In still other embodiments, the patient has a condition characterized by paralysis of the gut (e.g., paralysis of peristaltic movements of the bowel). In these embodiments, without wishing to be bound by theory, CO can act as a neurotransmitter to stimulate peristaltic contractions to treat or ameliorate the condition. In some embodiments, the patient may have paralytic ileus (e.g., following abdominal trauma or surgery), Hirschprung's Disease, or toxic megacolon.

In some embodiments, the patient is diagnosed or considered at risk for necrotizing enterocolitis, which is a condition typically seen in premature infants. The timing of its onset is generally inversely proportional to the gestational age of the baby at birth. Initial symptoms include feeding intolerance, increased gastric residuals, abdominal distension and bloody stools.

In certain aspects, the invention provides carbon monoxide therapeutic regimens to reduce the incidence of organ transplantation failure, including preventing, ameliorating, or treating acute rejection, vascular rejection, chronic allograft rejection, and graft versus host disease. Historically, acute rejection may begin as early as one week after transplant, the risk being highest in the first three months, though it can occur months to years later. If an episode of acute rejection is recognized and promptly treated, organ failure can be prevented. Recurrent episodes can lead to chronic rejection. It is believed that the process of acute rejection is mediated by the cell mediated pathway. The term chronic rejection or chronic allograft rejection refers to a long-term loss of function in transplanted organs, for example, via fibrosis of the transplanted tissue's blood vessels. Graft-versus-host disease (GVHD) is a common complication following an allogeneic tissue transplant. It is commonly associated with stem cell or bone marrow transplant but the term also applies to other forms of tissue graft. Specifically, in GVHD immune cells in the tissue graft recognize the recipient as "foreign." The transplanted immune cells then attack the host's body cells. In various embodiments, the recipient is a recipient of organ or tissue selected from kidney, liver, lung, pancreas, heart, bone marrow, intestinal tissue, and skin.

By receiving CO therapy, either in the first one to three months after transplant surgery or even with continued treatment (as described in detail herein), acute rejection of the organ or tissue can be avoided, or ameliorated, optionally together with immunosuppressive therapy. In these or other embodiments, the likelihood or progression toward chronic rejection is also reduced.

In some embodiments, the patient is a kidney transplant recipient. In some embodiments, the regimen prevents, ameliorates, or treats delayed graft function after kidney transplantation. In various embodiments, the invention provides for increased transplantation success with types of organ donations that have been statistically less successful in avoiding DGF or long term graft survival, thereby increasing the availability of acceptable donor organs.

In particular, DGF after kidney transplantation may be correlated to the use of expanded criteria donors (ECD) and donation after cardiac death (DCD). See, Siedlecki et al., *Delayed Graft Function in the Kidney Transplant Am J Transplant* 11(11):2279-2296 (2011). In some embodiments, the donor organ (e.g., kidney) is from a deceased donor. In some embodiments, the organ donation was after cardiac death, which has shown high incidence of DGF. In still other embodiments, the donation (e.g., kidney donation) was after brain death, which also shows a high incidence of DGF, in part due to the donor's inflammatory state. In some embodiments, the donor was brain dead for at least about 10 hours, at least about 15 hours, or at least about 24 hours before organ procurement.

In some embodiments, the CO regimen described herein allows for the use of expanded criteria donors (ECD), with lower incidence of DGF. Expanded Criteria Donor is defined as a donor over the age of 60, or a donor over the age of 50 with at least two of: a history of high blood pressure, creatinine of >1.5, or death from stroke. In some embodiments, the donor is over 60 years of age, over 70 years of age, or over 75 years of age.

In accordance with the invention, various organ preservation methods may be employed, and these may include the use of CO ex vivo to enhance preservation. For example, the inclusion of CO (e.g., 50-2000 ppm) in the storage media in which organs to be transplanted are stored may substantially reduce the likelihood of oxidative damage to the organs during storage and substantially enhances the storage time that organs to be transplanted may be safely stored without suffering irreversible oxidative damage. Thus, in this aspect, an effective amount of CO is bubbled into storage media (with or without $O_2$, NO, $N_2$, and/or other gases) either before or preferably when an organ is first placed in the media or shortly thereafter.

In some embodiments, CO is included in the preservation/storage media at from about 50 to 2000 ppm, or 50 to 1000 ppm, or 50 to 500 ppm. Generally, cold preservation is used to reduce cellular metabolic rate and thereby reduce organ damage. Adenine-containing cold preservation buffer may be used, as well as lactobionate/raffinose solution or Histidine-Tryptophan Ketoglutarate. The donor organ may undergo machine perfusion, which may involve oxygen supplementation (with or without $O_2$, NO, $N_2$, and/or other gases). Siedlecki et al., *Delayed Graft Function in the Kidney Transplant Am J Transplant* 2011. Various storage or preservation media may be employed, with or without CO supplementation, including but not limited to Celsior solution, Perfadex, Euro-collins, and modified Euro-collins.

In various embodiments, the donor organ was preserved (with CO) for more than about 5 hours, more than about 8 hours, more than about 10 hours, more than about 16 hours, or more than about 24 hours before the transplant procedure.

In various embodiments, for example with respect to organ transplantation, the patient may receive CO therapy a plurality of times during the peri-operative period. Alternatively or in addition, the patient may receive inhaled CO therapy substantially before and/or substantially after the perioperative period. In these or other embodiments, the patient may receive CO therapy intraoperatively. In some embodiments, CO is delivered intraoperatively, with one or more or a pre-operative or post-operative CO regimen.

For example, the recipient may be pre-conditioned with CO therapy. The recipient may receive CO therapy from several weeks, to several days, to one or more hours prior to the organ transplant operation. In some embodiments, the recipient initiates a CO regimen, as described herein, from 1 to 8 weeks, or from 1 to 6 weeks, or from 1 to 4 weeks, or 1 or 2 weeks leading up to the transplant procedure. In some embodiments, CO dosing over time is beneficial in reducing baseline inflammation and/or induction of HO-1 activity. In other embodiments, the recipient receives inhaled CO therapy over the course of about one week leading up to transplantation. In total, prior to surgery, the patient may receive from 1 to about 20, or from 1 to about 15, or from 1 to about 10 administrations of CO therapy (e.g., in the range of 3 to 10 administrations prior to surgery). In these or other embodiments, inhaled CO is administered from 1 to 3 times on the day of transplantation, including from about 0.5 to about 5 hours prior to surgery. In some embodiments, CO is administered for about 1 to 3 hours leading up to the surgery. In some embodiments, each administration of CO is separated by at least about 6 hours, at least about 12 hours, at least about 24 hours, at least about 36 hours, at least about 48 hours, or at least about 60 hours.

In these or other embodiments, the patient receives post-operative CO therapy. For example, in some embodiments, the recipient receives CO therapy for from 1 to 8 weeks, or from 1 to 6 weeks, or from 1 to 4 weeks, or 1 or 2 weeks after the transplant procedure. In other embodiments, the recipient receives the CO regimen over the course of one week, or from 1 to 3 or 1 to 4 days after transplantation. This may involve from 1 to about 20, or from 1 to about 15, or from 1 to about 10 administrations of CO (e.g., from 3 to about 10 administrations of inhaled CO). In these or other embodiments, inhaled CO is administered from 1 to 3 times within the first 24 hours after transplantation, including being initiated at from 0.5 to 5 hours post-surgery. In some embodiments, each administration of CO is separated by at least about 6 hours, at least about 12 hours, at least about 24 hours, at least about 36 hours, at least about 48 hours, or at least about 60 hours.

In these or other embodiments, the patient may receive intraoperative CO delivery. For example, in some embodiments, CO is administered for about 1 hour leading up to the surgery, and optionally during surgery, and optionally from one to ten times after surgery (within the first one or two weeks after surgery).

In some embodiments, the patient is identified as having or at risk of having DGF or acute rejection post-surgery, and CO therapy is administered post-operatively. For example, patients may be identified as at risk of DGF by determining the presence of slow graft function, or ischemia and/or antibody induction around the time of transplantation, or other method. For example, in the case of kidney transplantation, the patient may exhibit slow graft function, where glomerular filtration rate and serum creatinine do not achieve normal levels but remain below that warranting dialysis.

In some embodiments, the patient receives inhaled CO from 2 to about 10 times during the perioperative period. In some embodiments, the patient receives inhaled CO from 2 to about 5 times during the perioperative period. In some embodiments, the patient receives the first two administrations of inhaled CO separated by from about 36 to about 60 hours, the first at the time of transplantation. In still other embodiments, the patient receives intermittent dosing (e.g., with peak levels of ≤10% carboxyhemoglobin) after the perioperative period for prophylactic treatment to prevent DGF. For example, after the perioperative period, the patient may receive inhaled CO therapy at least once per day (e.g., 1-3 times per day), at least once per week (e.g., 1-5 times per week), or at least once per month (e.g, 1-10 times per month). In some embodiments, the patient receives CO therapy from about 1 to about 5 times weekly (e.g., 1, 2, 3, 4, or 5 times per week), or receives CO therapy about every other week, or about once or twice per month.

In the case of prophylactic or attenuating therapy for chronic conditions, either for native or transplanted organs or tissues, the patient may receive inhaled CO therapy at least once per day, at least once per week, or at least once or twice per month. For example, the patient may receive inhaled CO therapy about daily, about once or twice weekly, or from 1-5 times monthly. In some embodiments, the patient receives CO therapy from about once to about five times weekly (e.g., 1, 2, 3, 4, or 5 times per week), or receives CO therapy about every other week.

In some embodiments, the patient has one or more markers of a fibrotic condition. For example, in some embodiments, the patient has MMP1, MMP7, and/or MMP8 blood levels (e.g., peripheral blood, serum, or plasma, etc.) that are substantially elevated compared to healthy controls. For example, in some embodiments, the baseline MMP7 levels are above about 12 ng/ml, or above about 10 ng/ml, or above about 8 ng/ml, or above about 5 ng/ml, or above about 3 ng/ml. In accordance with various embodiments, MMP7 levels are tested periodically as a measure of improvement, and are maintained at below about 8 ng/ml, and preferably below about 5 ng/ml or below about 3 ng/ml. For example, MMP7 levels may be substantially maintained at about control or subclinical levels with inhaled CO therapy. Alternatively, a fibrotic condition and/or progression of a fibrotic condition can be monitored by galectin levels (e.g., one or more of isoform 1, 2, 3, 4, 7, 8, 9, and 10) and/or soluble collagen fragments in the circulation (e.g., Collagen types I, II, III, and/or IV), or other marker of fibrosis. Improvement in markers can be based upon a reduction from a baseline measurement taken prior to initiation of a CO regimen.

During each treatment, CO gas may be administered for about 10 minutes to about 5 hours per dose, such as about 30 minutes per dose, about 45 minutes per dose, about one hour per dose, or about two hours per dose. The duration of treatment in some embodiments reflects the duration that the target carboxy-hemoglobin level is maintained during the administration (e.g., the steady-state level). In still other embodiments, the duration reflects the entire administration protocol, including the time period to reach the target CO level.

There are a number of markers that can be used to monitor or measure CO uptake in the patient. Although the best-known reaction of CO incorporated in a human or animal body is the formation of carboxyhemoglobin (CO-Hb), CO can also interact with other biological targets such as myoglobin (e.g., carboxymyoglobin) and cytochrome oxidase. Thus, in various embodiments one or more carboxy protein levels are monitored, including but not limited to CO-Hb or CO-myoglobin. In some embodiments, CO complexed with blood cells or tissue cytochromes is measured. Alternatively, oxygen level or $pO_2$ in combination with CO-Hb may be used as a marker or end-point for CO administration. In still other embodiments, blood pH is monitored as a marker of CO uptake. In still other embodiments, exhaled CO or NO can be used to estimate CO blood levels during CO administration.

In some embodiments, the duration and/or dose of CO is determined by continuous or periodic monitoring of serum oxyHb and/or CO-Hb. For example, CO may be administered until the patient reaches about 6%, about 7%, about 8%, about 9%, about 10%, about 11%, about 12%, about 13%, about 14%, or about 15% CO-Hb, with this target optionally maintained for a period of time.

In various aspects and embodiments, the invention provides methods of safely delivering therapeutic levels of CO to a patient, with such methods being suitable for acute and chronic treatment. For example, for chronic treatment, the methods allow for safe delivery of therapeutic levels of CO on a substantially regular basis. For example, the frequency of administration can be between once monthly to about four times weekly, to prevent, arrest, delay, or attenuate the progression of chronic processes that lead to impaired function of transplanted or native organs or tissues.

In various embodiments, CO-Hb is used as a marker to guide the CO administration regimen and/or the CO dosing protocol. For example, CO-Hb may be tested before, during, or after CO administration, using a blood test, percutaneous device, or other device such as a pulse oximeter. CO-Hb in various embodiments can be used as a marker for the end-point of a CO dose, and/or used to establish a CO-dosing protocol for a patient. In various embodiments, during CO administration CO-Hb is maintained below about 20%, below about 15%, below about 12%, below about 10%, or below about 8%. In some embodiments, each CO administration targets a CO-Hb endpoint, which may be below about 15%, below about 12%, below about 10%, or below about 8%, or may be about 7%, about 8%, about 9%, about 10%, about 11%, or about 12%. For example, the CO-Hb endpoint may be between about 8% and about 12% (e.g., about 10%). In some embodiments, CO-Hb is maintained at the target level for a period of time during administration by adjusting the CO dose to achieve a steady state CO level. The steady state level may be maintained for about 30 minutes, about 45 minutes, about 1 hour, about 2 hours, or about 3 hours. In some embodiments, for example in the case of hospitalized patients or more advanced stages of disease, CO-Hb is maintained at a level of from about 5% to about 15% persistently with intermittent administration of CO. In some embodiments, CO-Hb is maintained at about 8-12% in some embodiments. For example, the frequency of administration may be set to maintain a base CO-Hb level over time. This level may be substantially maintained for at least about one week, at least about two weeks, or at least about one month.

In some embodiments, the CO administration protocol comprises at least two concentration levels of CO gas; a relatively high level of CO to quickly reach a target CO blood level (e.g., as measured by CO-Hb level), and a maintenance level of CO to maintain the CO or CO-Hb endpoint for a period of time to provide the desired therapeutic effect. In such embodiments, the administration is safe and controlled to avoid toxic and/or undesired CO exposure, while reducing the time of the administration procedure considerably. Further, for the treatment of certain chronic conditions, it may be necessary to maintain a certain level of CO in the blood for a period of time to achieve the desired therapeutic effect.

In various embodiments, the administration process comprises delivering CO gas at a constant alveolar concentration to a patient via inhalation. The delivery of CO gas to the patient reaches a steady-state during treatment, where equilibrium between the alveolar concentration and the patient's CO-Hb level is achieved. The steady-state uptake enables control of the delivered CO dose, and allows for safe administration of CO gas. In some embodiments, the steady-state mode (e.g., for maintaining a target CO-Hb level within about 6% to about 12%) is continued for from about 15 minutes to about 3 hours, or from about 30 minutes to about 2 hours, or from about 30 minutes to about 1 hour (e.g., about 30 minutes, about 45 minutes, about 1 hour, about 1.5 hours, or about 2 hours).

There are many factors that can affect the uptake of carbon monoxide by a patient via inhalation. For example, some factors are related to characteristics associated with the patient, including but not limited to: changes in alveolar-capillary membrane (i.e. membrane factor); the pulmonary capillary blood volume; hemoglobin concentration; and total blood volume. Other factors associated with the patient can include CO back-pressure from endogenous CO production, and prior patient exposure to CO. The influence of these patient-related factors can vary based on the relative health of the patient. There are also non-patient factors that can affect the rate and extent of uptake by the patient, namely factors that can be controlled or at least influenced by the nature of the CO delivery system. For example, the most important of these factors is the alveolar concentration of CO. The alveolar concentration is the concentration of CO present in the gas in a patient's lungs during treatment. The alveolar CO concentration is a function of the movement of gases in the lung and also the partial pressure of CO in the gases in the lung. While the patient-related factors of CO uptake can be difficult to measure, the alveolar concentration of CO can be held relatively constant through the use of the system and methods described herein. Therefore, by controlling the alveolar concentration of CO, fluctuations in the rate of CO uptake can be minimized or avoided.

The uptake of CO in humans is mostly dependent upon the concentration of the inhaled gas and the diffusing capacity of the lungs. The formation of HbCO on the basis of CO exposure has been described in a physiologically-based single-order pharmacokinetics model, and is referred to in the literature as the Coburn-Foster-Kane equation (i.e. the CFK equation or CFKE).

CFK Equation:

$$\frac{A[HbCO]t - BVco - PIco}{A[HbCO]0 - BVco - PIco} = \exp\left(-\frac{tA}{VbB}\right)$$

Where:
$A = PC_{O2}/M[HBO_2]$
$B = 1/DLco + P_L/V_A$
M=ratio of the affinity of blood for CO to that for $O_2$
$[HbO_2]$=ml of $O_2$ per ml of blood
$[HbCO]_t$=ml of CO per ml of blood at time t
$[HbCO]_0$=ml of CO per ml of blood at the beginning of the exposure interval
$PC_{O2}$=average partial pressure of oxygen in the lung capillaries in mmHg
$V_{CO}$=rate of endogenous CO production in ml/min
$DL_{CO}$=diffusivity of the lung for CO in ml/min×mmHg
$P_L$=barometric pressure minus the vapor pressure of water at body temperature in mmHg
Vb=pulmonary blood volume
$PI_{CO}$=partial pressure in the inhaled air in mmHg
$V_A$=alveolar ventilation in ml/min
t=exposure time in min
exp=2.7182, the base of natural logarithms raised to the power of the bracketed expression According to the CFK equation, the time to reach an equilibration point between the alveolar concentration of CO and the body's stores can be relatively long, on the order of many hours in a healthy human (see, for example, FIG. 2 of Peterson J E, et al., *Predicting the carboxyhemoglobin levels resulting from carbon monoxide exposures*, J Applied Physiol Vol. 39(4):633-638 (1975), reproduced here as FIG. 1. In a patient with diseased lungs, the time to reach a steady-state condition, that is, where the blood Hb-CO level reaches a plateau, can take even longer. However, if the HbCO level gets too high the patient can experience severe adverse effects or even death. Further, the concentration of CO in inhaled air can greatly affect the time needed to reach the desired steady-state concentration. For example, with a CO alveolar concentration of 25 ppm, it can take about 20 hours to reach an equilibration point, while at 1000 ppm, the time to reach steady-state can be shortened to between 2 and 3 hours. However, predicting equilibration points based on the CFK equation may be difficult, especially when Hb-CO measurements lie on the steeper region of a curve and all of the physiologic variables are unknown or cannot easily be measured.

The surface area of the lungs is a huge surface area, and has the greatest influence over how much and how fast CO is absorbed by the blood. If the alveolar surface (i.e., membrane) gets thick, it slows CO diffusion. If it gets destroyed and there is less surface area, total uptake is slowed. Of the variables from the CFK equations, only $DL_{CO}$, starting HbCO, inspired CO, and time are important because the rest of them at steady-state conditions do not change much or have much impact. For example, it is sufficient to plug in reasonable estimates for the patient (e.g., average values for the patient's age, sex, and/or weight) and leave them as constants.

In some embodiments, the CO dose is controlled by measuring inhaled CO uptake by the patient at a select CO dose for a select period of time. The measurement of CO uptake allows for close approximation of diffusivity of the patient's lungs for CO ($DL_{CO}$), which in turn allows personalized correlation between CO dose, exposure time, and CO levels in the blood (e.g., CO-Hb level). According to these embodiments, the less significant physiologic variables can be bundled into a single unmeasured factor using constants, and the actual CO uptake calculated to allow close approximation of the only really important physiologic variable, which is $DL_{CO}$. Thus, CO-Hb level can be sufficiently controlled to rapidly achieve the desired CO-Hb target, and then maintain that target for a desired duration.

In various embodiments, relatively high CO concentrations (e.g., at least 500 ppm, or at least 600 ppm, or at least 800 ppm, or at least 1000 ppm, or at least 1500 ppm, or at least 2000 ppm, or at least 2500 ppm) are administered to the lungs in the initial period of the procedure in order to quickly achieve the desired CO-Hb level in the patient. Because all of the unknown physiologic influencers of the formation of CO-Hb are unknown values during this portion of the procedure, CO-Hb levels in the patient may be continuously or intermittently monitored to ensure that the patient's CO-Hb level does not exceed a safe level. In some embodiments, CO-Hb is measured exactly twice, a baseline CO-Hb and a second measurement within about 10 minutes to about 30 minutes of CO administration. Since there may be a fine line between safe and harmful levels of carboxyhemoglobin, it can be important in some embodiments to appropriately time CO-Hb testing, so as to accurately predict Hb-CO endpoints to avoid CO toxicity.

Thus, in some embodiments, baseline CO-Hb is measured, and then the CO-Hb is measured at a known time point during CO exposure, and then by inserting the inspired CO into the equation, the equation is rearranged and solved for $DL_{CO}$. This $DL_{CO}$ approximation (which is only slightly influenced by the unmeasured and bundled physiologic constant parameters) is plugged back into the rearranged equation and solved for the final CO-Hb at any time point going forward using the new starting CO-Hb. The computer system (e.g., described further below) is programmed to perform these calculations, based on CO-Hb values input by a user or input automatically through communication with sensor or diagnostic instruments. Other values, such as desired CO-Hb target and duration, can likewise be input by the user. Similar relationships based on other proxy's for CO level (e.g., other than CO-Hb) can be used.

The physiologically-based pharmacokinetics model associated with the CFK equation does not account for the existence of multiple physiologic compartments in the body, that is, it does not account for physiologic compartments other than the lungs. Benignus explored the arterial versus venous response to inhaled carbon monoxide [Benignus et al., 1994, *J Appl Physiol.* 76(4): 1739-45]. According to Benignus, not all subjects responded alike, and while the majority of subjects followed the CFK equation, some subjects substantially deviated from the CFK model. Benignus determined that antecubital venous Hb-CO levels were over-predicted and arterial Hb-CO levels were under-predicted, indicating the presence of at least one additional physiologic compartment. Further, Bruce et al. [2003, *J Appl Phys.* 95(3):1235-47] modeled Hb-CO responses to inhaled CO, and identified five compartments that can be considered in a model: lungs (alveolar), arterial blood, mixed venous blood, muscle tissue, and other soft tissues.

Therefore, in some embodiments, the CO administration protocol as described further comprises modeling inhaled CO uptake by considering at least one additional compartment other than the lungs, such as one or more of: muscle tissue, other soft tissue, arterial blood, and/or venous blood. In some embodiments the protocol comprises calculating a CO dose using the percentage of muscle mass in a subject as a variable. Conventional methods for CO administration use only body weight as a factor for dosage determination, which may result in missing other relevant factors. For example, by using only body weight, differences in the level of muscle mass between men and women may not be considered when specifying a CO dose amount for therapeutic treatment, even though differences in muscle mass can result in significant differences in CO uptake and/or storage.

Further still, systems based on pulsed dosing may miss additional relevant factors. In systems based on pulsed dosing, a volume of CO that is a fraction of the total dose per minute is set by the device operator and injected into the breathing circuit. The volume fraction injected is typically determined by the patient respiratory rate, so that equal portions of the specified dose are delivered with each breath. The dose per breath is typically fixed, independent of the size of the tidal volume, which is the volume of air displaced between normal inspiration and expiration. Therefore, when such a fixed CO volume is injected into a varying inspired volume of air, the concentration of CO in the alveoli will vary inversely to the size of the breath. Accordingly, at larger tidal volumes, the alveolar concentration of CO will fall and the uptake of CO will also fall. In general, patients do not breathe at a fixed tidal volume for every breath. There is a natural variation on a breath-by-breath basis, and, in addition, any variation in activity by a patient, e.g. at night when the patient is asleep, can change the alveolar concentration of CO in a pulsed-dose system. These variations can lead to significant variation in tidal volumes, which can result in a significant change in Hb-CO levels in the patient during treatment.

Accordingly, in a pulse-based dosing system and method of CO administration, the alveolar concentration is not constant. The alveolar concentration of one constituent in a mixture of gases is a function of the partial pressure of the constituent gas, i.e. the proportion of the constituent gas to all of the other gases in the mixture multiplied by the barometric pressure (i.e., less water vapor). For example, consider a system with pulsed addition of CO gas in which a patient inhaled a 25 mL bolus of a gas mixture containing 0.3% CO (3000 ppm) that was added to 700 mL of breath of air. If the patient had a functional residual capacity (FRC), i.e. the volume of air in the lungs at the end of a normal breath, of 1 liter, then when the inspired gas was mixed in the alveoli, the inspired gas would have been diluted to about 1.4 percent of the bolus concentration (25/(25+700+1000), or 43 ppm (a partial pressure of 3 mmHg at sea level). However, if the FRC was 400 mL instead of 1000 mL, the CO concentration would rise to almost 1.8%, or 53 ppm (3.7 mmHg). This change represents a 23 percent increase in CO concentration that could result in a 2 percent increase in the blood CO-Hb level, which could be enough to produce adverse health effects. Accordingly, the greater the delivered dose in a pulse-based system, the greater the potential variability. In acute disease states and in particular in patients on mechanical ventilators, even larger changes in FRC could be present, and such changes could result in even more significant swings in partial pressure that would affect uptake and might compromise patient safety. Alternatively, when the inspired gas is precisely premixed and delivered as a constant concentration, independent of respiratory rate, FRC, or tidal volume, there is little or no fluctuation in alveolar gas concentration.

In certain aspects, the methods and systems provide a constant alveolar concentration of carbon monoxide. In these aspects, the protocol safely delivers a specified concentration of CO, for example in ppm levels, to either mechanically-ventilated or spontaneously breathing patients. The use of constant alveolar concentration dosing assures that the patient's alveolar concentration will remain the same, and that the patient's Hb-CO level will reach a steady state during the treatment and enables relatively easy adjustments for better control of the delivered dose. Thus, in some embodiments, the concentration of CO is adjusted during treatment to maintain a constant alveolar concentration.

In related aspects, the invention further provides methods and systems for predicting CO-Hb level during CO administration. Considering that inter-patient differences, for example diffusing capacity, cardiac output, endogenous carbon monoxide production and pulmonary capillary blood volume, can result in significant differences in carboxyhemoglobin levels for the same dosage level of CO, a method and system to accurately predict the carboxyhemoglobin level at any point in time of exposure would be of great value. In some embodiments, the administration process (or the personalization of the CO regimen) comprises a reverse calculation of $DL_{CO}$ (the Diffusing capacity or Transfer factor of the lung for carbon monoxide), to more accurately predict the desired CO dose. For example, a first concentration of CO is administered for a period of time, such as from 5 minutes to about 30 minutes, such as from about 10 minutes to about 25 minutes, or from about 15 minutes to about 25 minutes (or for about 10 minutes, about 15 minutes, about 20 minutes, or about 30 minutes in various embodiments). At the end of that period CO-Hb is measured. From the actual measurement, $DL_{CO}$ can be calculated from the CFK equation by substitution and solving for $DL_{CO}$ because all of the other variables are known, and $DL_{CO}$ accounts for the balance of the difference from predicted value. With the physiologically derived $DL_{CO}$ (including the miscellaneous physiologic factors), one can accurately predict the CO-Hb using the CFK equation at any point in time at the same inspired CO, or make a change in inspired CO and predict the CO-Hb at any other point in time.

In some embodiments, a measured CO level (e.g., CO-Hb level) is input into the delivery system by a user or an associated CO-Hb measuring device, and the time and further CO dose to reach the desired end-point is automatically adjusted by the delivery system.

For example, in some embodiments a first high concentration of CO is administered to the patient for from 5 minutes to about 30 minutes (as described above), and CO-Hb is measured either using an associated device or by drawing blood for testing. From the CO-Hb measurement, the dose of inhaled CO to reach the desired CO-Hb endpoint at a particular time is determined. This determination can comprise calculating $DL_{CO}$. In some embodiments, CO-Hb is measured after about 15 to about 25 minutes of the initial CO dose (e.g., after about 20 minutes of the initial CO dose), to allow saturation of physiological compartments such as muscle, thereby providing a more accurate estimate of the CO dose needed to reach the desired CO-Hb endpoint. Once the patient is predicted to reach the CO-Hb endpoint, the CO dose is adjusted to the dose determined to maintain a steady-state CO-Hb level. These predictions can be made using relationships defined by the CFK equation as disclosed herein.

In some embodiments, each administration of CO is a predetermined regimen to reach a selected CO-Hb endpoint (e.g., steady-state concentration), and maintain that endpoint for a period of time. This regimen may be empirically tested for the patient, and determined based on a set of criteria, and then subsequently programmed into the delivery system. In these embodiments, cumbersome and invasive blood tests are avoided, which further renders the treatment suitable for home care. Further, in some embodiments, the method or system does not rely on continuous CO or CO-Hb measurements, but relies on a specified regimen personalized for the patient. Thus, in some embodiments, CO dosing scheme (e.g., ppm over time, including steady-state administration steps) is determined in a personalized manner in a clinical setting with CO-Hb testing (e.g., blood test), and $DL_{CO}$ calculation, and the selected dosing schedule used going forward (either in the clinic or outpatient setting) without CO-Hb monitoring. In some embodiments, the CO-Hb is tested after administration at least once per year, or once every 6 months, or every other month, or once a month, to ensure that the dosing regimen remains appropriate for the patient, based on, for example, improving or declining health (e.g., lung function). In some embodiments, a less invasive pulse oximeter can be used to monitor CO levels when using a personalized regimen as described herein.

In various aspects, the invention uses systems to reliably control the CO administration process. For example, the methods may employ a CO dosing system to regulate the quantity of carbon monoxide which is delivered from a carbon monoxide source to the delivering unit. In various embodiments, the system comprises a sensor that determines the concentration of carbon monoxide in the blood of the patient, including spectroscopic or other methods, and/or means to measure carbon monoxide in the gas mixture expired from a patient (e.g., by spectroscopic methods or gas chromatography). The system may further comprise a control unit for comparing the actual CO blood concentration with a preset desired value, and subsequently causing the dosing unit to regulate the amount of carbon monoxide delivered to the patient to obtain a concentration in the patient's blood corresponding to the preset desired value. The control unit may perform a program control, a sensor control, or a combined program/sensor control.

CO-Hb levels can be determined by any method. Such measurements can be performed in a non-invasive manner, e.g., by spectroscopic methods, e.g., as disclosed in U.S. Pat. Nos. 5,810,723 and 6,084,661, and the disclosure of each is hereby incorporated by reference. Invasive methods which include the step of taking a blood sample, are employed in some embodiments. An oxymetric measurement can be performed in some embodiments, e.g., as disclosed in U.S. Pat. No. 5,413,100, the disclosure of which is hereby incorporated by reference.

There is an equilibrium regarding the distribution of carbon monoxide between blood and the respired gas mixture. Another method for determining the blood concentration of CO is the measurement of the carbon monoxide concentration in the expired air of a patient. This measurement may be done by spectroscopic methods, e.g., by ultra-red absorption spectroscopy (LIRAS), or by gas chromatography. This method of determination is well-established in medical art for the determination of the diffusing capacity of the lungs of a patient.

In some embodiments, the CO administration procedure comprises: setting a target Hb-CO level in the blood of the patient to be treated; administering CO gas at a first concentration while measuring the HbCO level in the patient's blood; reducing the CO level to a second concentration while continuing to monitor the patient's HbCO level; and continuing the administration of CO gas at the second concentration for a desired period of time, referred to herein as steady-state mode. For example, CO gas may be delivered via inhalation for a relatively brief initial period, for example 30 minutes to 1 hour, at an inhaled CO concentration of 100 to 2000 ppm until a desired blood level of CO is reached, for example about 7%, about 8%, about 9%, or about 10% HbCO, or other target concentration described herein. The time to reach the targeted value can vary significantly according to the patient's lung function or other factors, and methods for predicting the time required to reach the target blood level can be inaccurate or inconsistent. In some embodiments, the CO gas is delivered at an initial CO concentration until the desired HbCO level is achieved, instead of setting a specific time period for the CO delivery at the first CO concentration.

In one embodiment, the concentration of the CO being administered can be adjusted during administration based on real-time feedback from a pulse oximeter, or any other type of sensor that can directly or indirectly measure CO levels in a patient's blood. In such an embodiment, a target level of HbCO is set instead of setting a target level for the CO concentration being administered. The CO concentration can be automatically adjusted by the control system, depending on how the patient's HbCO level are responding to the CO concentration being delivered. For example, if the patient's HbCO level is increasing faster than expected, in comparison to pre-set reference parameters, the control system can lower the CO concentration being administered. In one embodiment, the control system uses the CFK equation to calculate the $DL_{CO}$ and then calculates the change in inspired CO concentrations.

In one embodiment, once the desired HbCO level in the patient's blood is achieved, CO gas is delivered to the patient at a second, lower concentration for a desired period of treatment time (e.g., from about 30 minutes to about 3 hours). This period of delivery at the second CO concentration is generally referred to herein as the steady-state delivery mode. In such embodiments, the CO concentration is reduced to the level needed to maintain the target CO-Hb level at steady-state without exposing the patient to toxic levels of CO.

Figure 2:
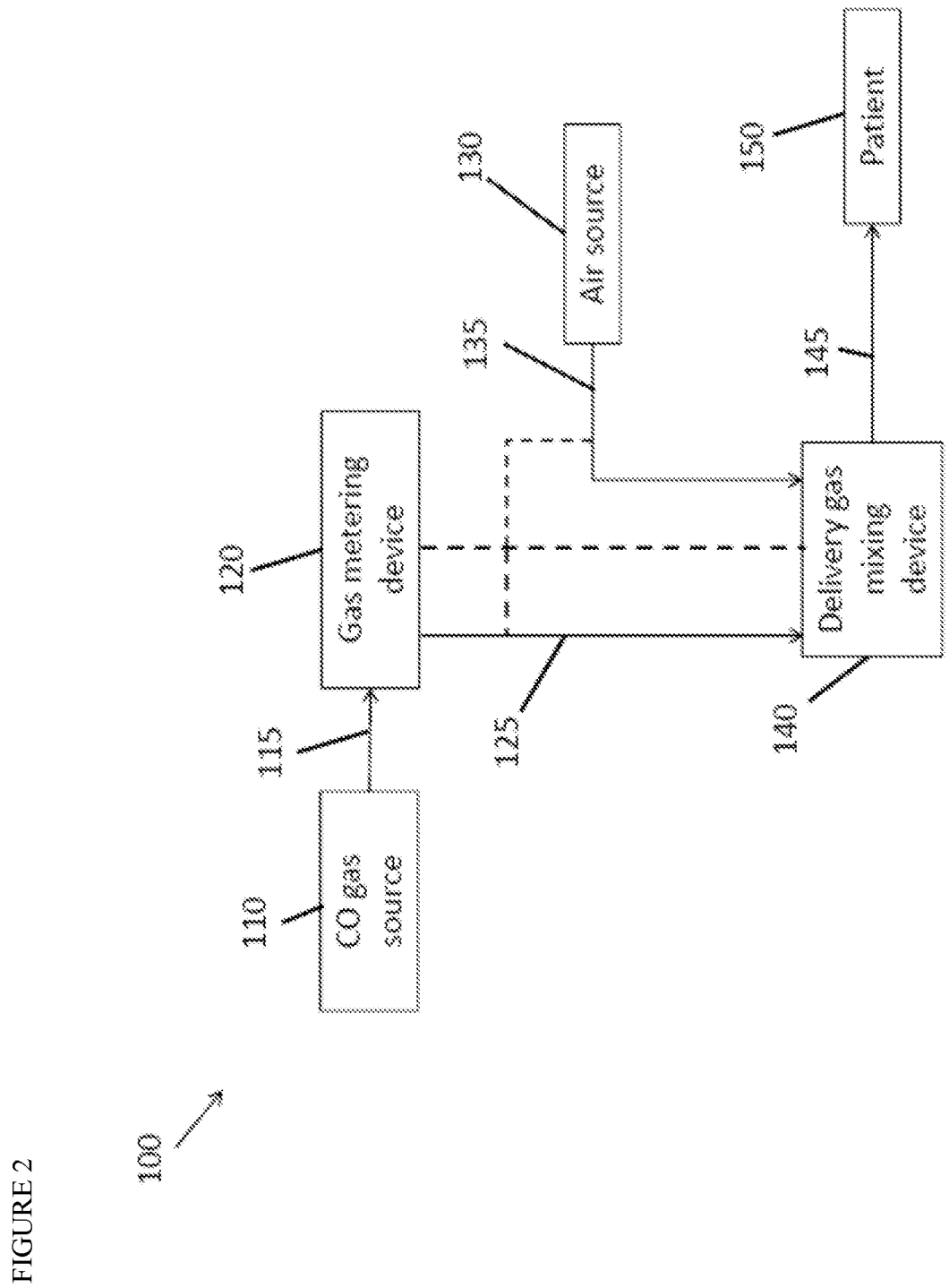
FIG. 2 illustrates a system for delivering CO in accordance with embodiments of the invention.
Figure 3:
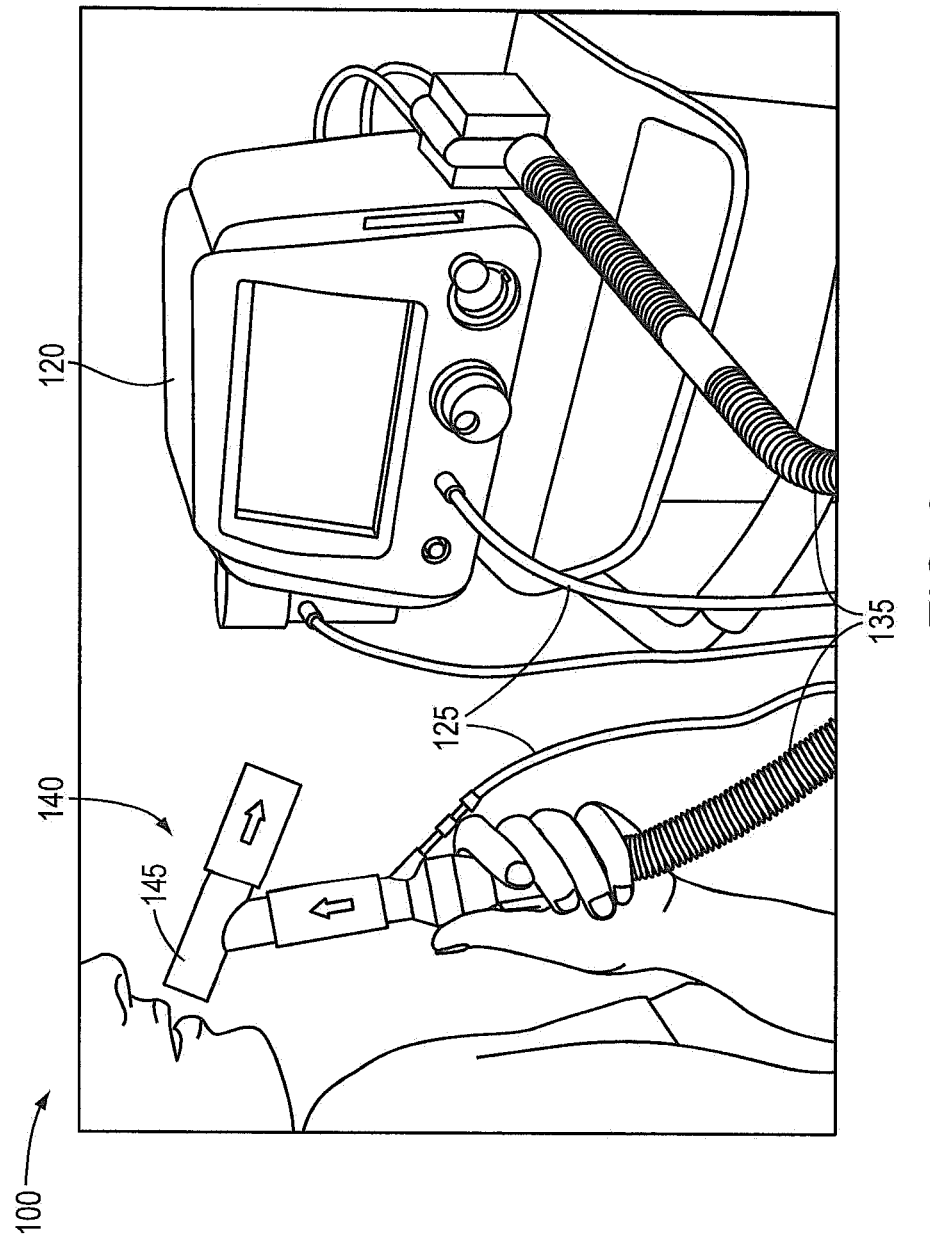
FIG. 3 depicts a system for delivering CO in accordance with embodiments of the invention.
Figure 4:
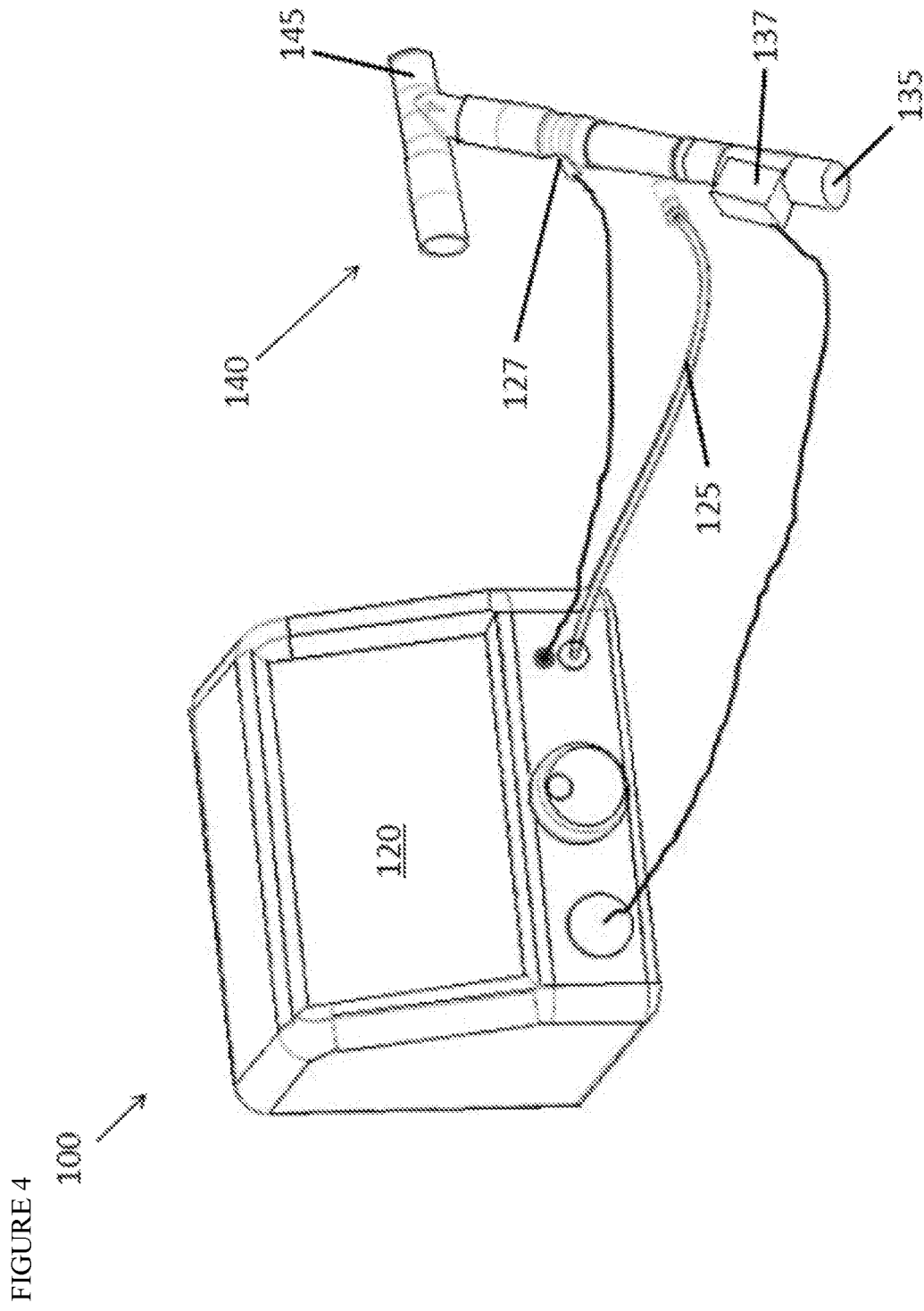
FIG. 4 illustrates the components of the system shown in FIG. 3.

An exemplary system for administering CO (100) is illustrated in FIG. 2-4. CO gas source (110) provides a gas mixture comprising CO to a metering device (120) through connection (115). Gas is mixed for delivery with air from air source (130), through connections (125) and (135) by a delivery gas mixing device (140). Mixed gas is delivered at a constant dose to the patient (150) through the delivery unit (145). Gas delivered to the patient is measured, for example, by a gas sampling port (127.) The system may further comprise a sensor measuring the flow of inspired room air, such as flow sensor (137). The system may further comprise a computer (e.g., Central Processing Unit and software) calculating $DL_{CO}$ based on CO-Hb values provided by user input or by connection to a CO-Hb sensor, and using other measured or input values for the CFK equation. The computer system may further provide for adjustment of the CO dose, by calculating (based on the $DL_{CO}$) the CO dose needed to reach a determined CO-Hb end-point in a specified duration. The computer system may further provide for determining a steady-state CO dose (e.g., that maintains a CO-Hb target). In some embodiments, the computer system controls a CO dosing regimen for a particular patient, by delivering a preset "high" amount of CO for a period of time, and then delivering a second lower dose of CO for a set duration. The high dose is determined in a clinical setting as the dose needed for the patient to achieve the desired CO-Hb end-point, and the second dose is determined clinically as a steady-state dose for the patient at the desired CO-Hb level. The required values in terms of CO concentration and duration of each dose can be input by the user (e.g., clinician).

In one embodiment, the system also comprises a pulse oximeter sensor that measures the HbCO level in a patient's blood. By non-limiting example, the pulse oximeter may be a Massimo RAD57 pulse oximeter. In another embodiment, the system comprises a sensor that measures the concentration of CO gas in the patient breathing circuit. In yet another embodiment, the system of the present invention comprises any type of sensor, other than a pulse oximeter, that is suitable for measuring or determining the HbCO level in a subject's blood. By non-limiting example, the sensor may be an Instrumentation Laboratories IL-182 CO-Oximeter.

In one embodiment, the system or method involves at least one central processing unit (CPU) or microprocessor for use in monitoring or controlling the CO gas concentration in the breathing circuit, the HbCO level in the patient, or any other variable necessary for operation of the system and methods described herein. In cases where it is desired to maintain a target HbCO level in a patient after the target level is reached, the device can automatically decrease the inspired CO gas concentration to the level required to maintain the desired steady-state HbCO concentration. The system may also comprise alarm or warning systems that can trigger warning messages or an automated shut-off, as described herein. In one embodiment, the measured HbCO values are continuously read by a CPU, and if the HbCO level rises above the pre-set threshold, the CPU can sound an alarm, display a warning message on the control unit, and/or send a signal to turn off delivery of CO gas to the breathing circuit.

In one embodiment, the system has at least two CPUs, wherein one CPU is used for monitoring the mixing of gases, for example air and CO, and the flow of CO-containing gas to the patient. In such an embodiment, a second CPU monitors other variables, for example the concentration of CO or oxygen in the inspired gas, the HbCO level measured by the pulse oximeter, or any other variable associated with the system. Further, the system may monitor the pressure in one or more gas source tanks feeding gas to the control system of the present invention, in order to assure that continuous therapy, i.e. gas flow, is provided.

In some embodiments, the system and method may further comprise other features, such as an alarm or warning system, an automatic shutoff feature, or an automated transition to a steady-state delivery mode. In one embodiment, when the CO-Hb level in the patient or the CO concentration in the breathing circuit is greater than the desired target level, the system of the present invention can institute an alarm or warning message to alert the operator, patient, or other person, of the deviation of the measured variable from a set point or target level. The alarm can be in the form of any visual, audio, or tactile feedback that would be suitable for informing a person of the deviation. In another embodiment, the system and method comprises an automatic shutoff feature that stops delivery of CO gas to the patient when the CO-Hb level or CO concentration in the breathing circuit exceeds a specified level.

In yet another embodiment, the system or method of the present invention comprises an automated transition to a steady-state delivery mode, wherein the concentration of CO gas being delivered to the patient is automatically reduced to a lower concentration once the desired level of CO-Hb in the patient has been achieved.

In various embodiments, the CO gas is administered at from 50 to 500 ppm CO for the steady-state mode. For example, the CO gas may be administered at from 50 to 300 ppm of CO, or from 50 to 150 ppm CO, or from 50 to 100 ppm CO in some embodiments for the steady-state mode. In some embodiments, CO gas is administered at less than 100 ppm. In other embodiments, the CO gas may be administered at from 100 to 400 ppm, such as from 200 to 300 ppm or from 250 to 300 ppm. In some embodiments, the CO gas is more than 200 ppm for steady-state mode.

In some embodiments, oxygen gas is delivered simultaneously or separately from CO to reduce CO toxicity or provide an enhanced effect. For example, oxygen gas may be delivered to the patient from 1 to 7 times per week, with or between CO treatments, and for from about 10 minutes to about 1 hour per treatment. When provided simultaneously, the $CO:O_2$ ratio may be from 100:1 to 1:100, or from 10:1 to 1:10, or from 5:1 to 1:5, or from 2:1 to 1:2 in some embodiments. In some embodiments, $O_2$ is delivered separately, and between CO administrations. For example, $O_2$ may be administered prior to CO administration by about 24 hours or less, or about 12 hours or less, or about 6 hours or less, or about 2 hours or less, or about 1 hour or less. In these or other embodiments, $O_2$ may be administered after CO administration by about 24 hours or less, or about 12 hours or less, or about 6 hours or less, or about 2 hours or less, or about 1 hour or less. $O_2$ may be administered before and after one or more CO administration(s). $O_2$ may be administered for a duration of from about 15 minutes to about 2 hours, including from about 30 minutes to about 1 hour.

In some embodiments, the CO therapy is provided to a patient that receives NO therapy, either simultaneously or separately. In some embodiments, without wishing to be bound by theory, NO therapy acts as a vasodilator to improve or enhance delivery of CO to organs and tissues.

Gaseous CO-containing compositions may be prepared by mixing commercially available compressed air containing CO (generally about 1% CO) with compressed air or gas containing a higher percentage of oxygen (including pure oxygen), and then mixing the gasses in a ratio which will produce a gas containing a desired amount of CO. Alternatively, compositions may be purchased pre-prepared from commercial gas companies. In some embodiments, patients are exposed to oxygen ($O_2$ at varying doses) and CO at a flow rate of about 12 liters/minute in a 3.70 cubic foot glass exposure chamber. To make a gaseous composition containing a pre-determined amount of CO, CO at a concentration of 1% (10,000 ppm) in compressed air is mixed with >98% O2 in a stainless steel mixing cylinder, concentrations delivered to the exposure chamber or tubing will be controlled. Because the flow rate is primarily determined by the flow rate of the O2 gas, only the CO flow is changed to generate the different concentrations delivered to the exposure chamber or tubing. A carbon monoxide analyzer (available from Interscan Corporation, Chatsworth, Calif.) is used to measure CO levels continuously in the chamber or tubing. Gas samples are taken by the analyzer through a portion the top of the exposure chamber of tubing at a rate of 1 liter/minute and analyzed by electrochemical detection with a sensitivity of about 1 ppb to 600 ppm. CO levels in the chamber or tubing are recorded at hourly intervals and there are no changes in chamber CO concentration once the chamber or tubing has equilibrated. CO is then delivered to the patient for a time (including chronically) sufficient to treat the condition and exert the intended pharmacological or biological effect.

In a preferred embodiment, the CO-containing gas is supplied in high pressure vessel containing between about 1000 ppm and about 100,000 ppm, such as about 3,000 to 8,000 ppm, such as about 4,000 to about 6,000 ppm, such as about 5,000 ppm, and connected to a delivery system. The delivery system can measure the flow rate of the air that the patient is breathing and can inject a proportionally constant flow rate of the CO-containing gas into the breathing gas stream of the patient so as to deliver the desired concentration of CO in the range of 0.005% to 0.05% to the patient to maintain a constant inhaled CO concentration.

In another embodiment, the flow of oxygen-containing air that is delivered to the patient is set at a constant flow rate and the flow rate of the CO-containing gas is also supplied at a constant flow rate in proportion to the oxygen-containing air to deliver the desired constant inhaled CO concentration.

The pressurized gas including CO can be provided such that all gases of the desired final composition (e.g., CO, He, Xe, NO, $CO_2$, $O_2$, $N_2$) are in the same vessel, except that NO and $O_2$ cannot be stored together. Optionally, the methods of the present invention can be performed using multiple vessels containing individual gases. For example, a single vessel can be provided that contains carbon monoxide, with or without other gases, the contents of which can be optionally mixed with the contents of other vessels, e.g., vessels containing oxygen, nitrogen, carbon dioxide, compressed air, or any other suitable gas or mixtures thereof.

Carbon monoxide compositions according to embodiments of the present invention can comprise 0% to about 79% by weight nitrogen, about 21% to about 100% by weight oxygen and about 1000 to about 10,000 ppm carbon monoxide. More preferably, the amount of nitrogen in the gaseous composition comprises about 79% by weight, the amount of oxygen comprises about 21% by weight and the amount of carbon monoxide comprises about 4,000 to about 6,000 ppm.

The amount of CO is preferably at least about 0.001%, e.g., at least about 0.005%, 0.01%, 0.02%, 0.025%, 0.03%, 0.04%, 0.05%, 0.06%, 0.08%, 0.10%, 0.15%, 0.20%, 0.22%, or 0.24% by weight. Preferred ranges of CO include 0.005% to about 0.24%, about 0.01% to about 0.22%, about 0.015% to about 0.20%, and about 0.025% to about 0.1% by weight. It is noted that gaseous CO compositions having concentrations of CO greater than 0.3% (such as 1% or greater) may be used for short periods (e.g., one or a few breaths), depending upon the application.

A gaseous CO composition may be used to create an atmosphere that comprises CO gas. The gases can be released into an apparatus that culminates in a breathing mask or breathing tube, thereby creating an atmosphere comprising CO gas in the breathing mask or breathing tube, ensuring the patient is the only person in the room exposed to significant levels of CO.

CO levels in an atmosphere can be measured or monitored using any method known in the art. Such methods include electrochemical detection, gas chromatography, radioisotope counting, infrared absorption, colorimetry, and electrochemical methods based on selective membranes (see, e.g., Sunderman et al., Clin. Chem. 28:2026 2032, 1982; Ingi et al., Neuron 16:835 842, 1996). Sub-parts per million CO levels can be detected by, e.g., gas chromatography and radioisotope counting. Further, it is known in the art that CO levels in the sub-ppm range can be measured in biological tissue by a midinfrared gas sensor (see, e.g., Morimoto et al., Am. J. Physiol. Heart. Circ. Physiol 280:H482 H488, 2001). CO sensors and gas detection devices are widely available from many commercial sources.

In some embodiments, the CO gas is administered to the patient by ventilator. In some embodiments, the CO gas is administered to the patient by an extracorporeal perfusion machine. In some embodiments, the patient is able to spontaneously breathe, and the CO gas is administered without any ventilation assistance.

In some embodiments, MMP7 levels are tested at least once weekly or once monthly, and the patient's treatment adjusted to substantially maintain MMP7 levels near subclinical levels (e.g., less than about 6 ng/ml or less than about 5 ng/ml or less than about 4 ng/ml), or to reduce other surrogate markers of fibrosis as described herein.

In some embodiments, the patient is undergoing therapy with one or more pharmaceutical interventions, which provides additional and/or synergistic benefits with the CO regimen.

For example, in some embodiments, the patient receives nitric oxide treatment, in addition to CO. In some embodiments, the patient is undergoing therapy with one or more of the following: one or more anti-inflammatory and/or immunomodulating agents, an anticoagulant, endothelin receptor antagonist, vasodilator, antifibrotic, cytokine inhibitor, and kinase inhibitor.

In various embodiments, the patient is undergoing therapy with a corticosteroid, such as prednisone or prednisolone. In some embodiments, the patient is undergoing treatment with azathioprine and/or N-acetyl-cysteine (NAC). In some embodiments, the patient is undergoing double or triple therapy with a corticosteroid (e.g., prednisone), azathioprine, and/or NAC. In still other embodiments, the patient is undergoing treatment with an antifibrotic, such as pirfenidone or Interferon-γ, or TNF-α inhibitor (e.g., etanercept). In these or other embodiments, the patient is undergoing treatment with one or more anticoagulants, such as warfarin or heparin. In these or other embodiments, the patient is undergoing treatment with one or more tyrosine kinase inhibitors, such as BIBF 1120 or Imatinib. In these or other embodiments, the patient is undergoing treatment with one or more phosphodiesterase inhibitors, such as sildenafil, or endothelin receptor antagonist, such as bosentan, ambrisentan, or macitentan. Other therapies that may provide synergistic or additive results with CO therapy include inhibitors of IL-13, CCL2, CTGF, TGF-β1, αvβb integrin, LOXL (e.g., neutralizing monoclonal antibody against IL-13, CCL2, CTGF, TGF-β1, αvβb integrin, LOXL).

In some embodiments, the patient is undergoing therapy with one or more pharmaceutical interventions, such as NO to assist in ischemic preconditioning, or other agents that reduce inflammation, induce vasodilation, or induce immunosuppression. Exemplary pharmaceutical interventions that can be synergistic with CO (or combination of gases described herein) in various embodiments include: Perfeindone, Nintedanib, Simtuzumab, STX-100 (Biogen), FG-3019 (Fibrogen), Tralokinumab, BMS-986020 (BMS), and Lebrikizumab, among others. In various embodiments, the patient undergoes additional therapy that acts as a TGF-β inhibitor, antioxidant, and/or anti-inflammatory; tyrosine kinase inhibitor suppressing FGFR, PDGFR and/or VEGFR; inhibitor of LOXL2 and/or TGF-beta signaling; inhibitor of TGF beta activation; inhibitor of Connective Tissue Growth Factor (CTGF), inhibitor of IL-13; or an antagonist of lysophosphatidic acid receptor.

Additional agents that are synergistic with CO in some embodiments, including therapy with an endothelin receptor antagonist, phosphodiesterase inhibitor, calcium channel blocker (e.g., dihyrdopyridine), and adenosine A1 receptor antagonist (e.g., rolofylline). Other recipient therapies that can be synergistic with CO in some embodiments include anti-inflammatory agents and apoptosis inhibitions (e.g., rPSGL-Ig, CXCR inhibitor, Diannexin).

In some embodiments, the recipient undergoes immunosuppressant therapy, such as with basiliximab, thymoglobulin (anti-thymocyte globulin or ATG), daclizumab, and/or alemtuzumab. In some embodiments, the patient undergoes chronic immunosuppression with a calcineurin inhibitor, sirolimus or everolimus, or Trimetazidine. In some embodiments, the patient is able to reduce or eliminate immunosuppressive therapy with CO treatment as described herein.

EXAMPLES

Example 1: Study of Back Calculation of DLCO and Predicting COHb at 60 Minutes To test the ability to predict CO-Hb levels at 60 minutes based on blood measurements of COHb at earlier time points, an experiment was performed in a *S. pneumoniae* model induced in four juvenile baboons. Using measured COHb levels after 10, 20, 30, 40, and 50 minutes of 200 ppm CO administration, a computer program generated in MATLAB (Mathworks) was used to back calculate the estimated $DL_{CO}$ (including unmeasured physiologic variables) using the CFK equation (Coburn et al. *JCI*, 43: 1098-1103, 1964; Peterson et al. *JAP*, Vol. 39, No. 4, 633-638, 1975). Then using the estimated $DL_{CO}$ and measured time point CO-Hb levels, the computer then used the CFK equation to predict the CO-Hb level after a 60 min. CO exposure. There was good correlation between the predicted and measured COHb levels (Table below). It was determined that this method can be used to predict the 60 min CO-Hb level with high accuracy ($R2=0.9878$) using the 20 min COHb level.

| Time Point (Min) | 60 Min predicted COHb minus actual COHb | SD | 95% CI |
|---|---|---|---|
| 10 | −0.777% | 1.07 | (−3.4, 1.8) |
| 20 | 0.28% | 0.43 | (−0.4, 0.97) |
| 30 | −0.05% | 0.18 | (−0.33, 0.23) |
| 40 | −0.13% | 0.06 | (−0.23, −0.03) |
| 50 | −0.11% | 0.05 | (−0.2, −0.02) |

Example 2: A Randomized, Single-Blind Placebo-Controlled Study to Evaluate the Safety and Efficacy of Inhaled Carbon Monoxide in the Prevention of Delayed Graft Function (DGF) in Allogeneic Renal Transplant Recipients Objectives:

A primary objective is to evaluate the safety and tolerability of Carbon Monoxide administered by inhalation in a concentration of 250 ppm intra-operatively at the time of renal graft reperfusion and in the immediate days post-transplant. CO will be administered for approximately 1 hour to achieve a target blood carboxyhemoglobin level (COHgb) of 8-10%. Safety and tolerability at the time of transplant will be assessed by the occurrence of Adverse Events (AEs) and by the monitoring of vital signs, blood oxygenation, serum hematology and chemistry, cardiac status by both telemetry (intraoperatively) and electrocardiograms (ECGs), and clinical evaluation of neurocognitive status by a battery of standard evaluation tools that assess concentration, reaction time, and memory.

Another primary objective is to evaluate the efficacy of CO by determining its impact on delayed graft function (DGF), measured in the week following transplantation.

Other objectives include: (1) Characterizing the pharmacokinetics (PK) of COHgb in renal transplant subjects following inhalation of CO; (2) evaluating the efficacy of inhaled CO by measuring creatinine clearance and the trajectory of estimated glomerular filtration rate (eGFR) improvement in the week following transplantation; (3) evaluating the association between safety and tolerability outcomes to inhaled CO doses and COHgb levels (as assessed by analysis of venous blood samples).

An additional objective is to assess the change in renal function post-transplant by serum blood urea nitrogen (BUN) and serum creatinine. Assess markers of renal ischemic reperfusion injury and DGF by measuring both urine and serum biomarkers in the week observation period post-transplant. These could include, (but not be limited to) urine IL-18 and NGAL (neutrophils gelatinase-associated lipocalin) levels as potential markers for the incidence of DGF. Other potential markers to evaluate or identify recipients at risk for DGF include mRNA expression profiles, miRNA serum or tissue profiles, the presence of certain SNPs, and/or the MRP2 gene or its expression.

Methods:

Patients scheduled to receive allogeneic transplants 18-70 years of age at participating centers will be the targeted population for this study. This study will be conducted as a single-blind, placebo-controlled, study. Participating subjects will be randomized to receive CO or placebo (room air) intraoperatively, with inhaled CO therapy to start intraoperatively at or just before the time of renal graft reperfusion. CO will be administered as 250 ppm CO blended into the patient's breathing circuit from a gas source containing 5000 ppm CO, 21% O2, balance Nitrogen mixture. Subjects will be dosed intraoperatively, supervised by the operative anesthesiologist, and will be administrated as the inhaled CO gas for approximately 1 hour to achieve a target carboxyhemoglobin level of 8-10%. Intraoperative dosing will be done while the patient is intubated.

On the second post-operative day, between 36 and 60 hours after kidney graft reperfusion, patients will be given a second inhaled CO or placebo dose using the same delivery system via mask or mouthpiece while breathing spontaneously. This dose will again be with 250 ppm of CO, 21% O2, balance nitrogen, for one hour, again targeting a blood COHgb level of 8-10%. A total of 200 subjects receiving cadaveric kidney transplants and fulfill the entry criteria will be allocated to receive CO or placebo. Follow-up visits will be planned for Day 7 (or assessment conducted in hospital, if the subjects remains in the hospital 7 days after transplant), Day 14, and 3 months after the administration of study drug.

A total of 200 subjects, allocated equally between the CO and placebo treatment arms, will be studied. Assessment of DGF, the primary efficacy outcome will occur at 7 days. Subjects will return for safety assessments for study purposes at 14 days, and again 3 months post-transplant. Efficacy assessments of renal function will occur at multiple times during the 7 days after transplant, and at the 14 day and 3 month follow-up visit.

These will include serum creatinine and BUN measurements, as well as creatinine clearance to estimate GFR.

Number of Subjects (Planned):

200 subjects receiving allogeneic cadaveric renal transplants will comprise the study population. One hundred subjects each will be randomly allocated to inhaled CO and placebo treatment.

Inclusion Criteria:

Subjects 18-70 years of age receiving cadaveric kidney transplants;

Subjects who were dialysis-dependent prior to transplant;

Subjects undergoing first renal transplant

Exclusion Criteria:

Subjects who had prior kidney transplant;

Subjects with history of malignancy within the prior 5 years, other than basal cell skin cancers;

Subjects with significant pre-transplant anemia, whose serum Hgb is consistently <10.0 g/dl;

Subjects who, in the opinion of the investigator, have unstable medical issues rendering them at significantly greater risk for adverse events in the peri-operative period;

Patients with significant pulmonary gas exchange compromise or conditions, such as interstitial lung disease or severe emphysema, and all subjects who consistently have baseline oxygen saturations on room air of <90%;

Subjects with baseline carboxyhemoglobin (CO Hgb) levels ≥2%;

Subjects whose body-mass index (BMI) exceeds 35;

Subjects receiving a kidney graft from a donor younger than 35 years old AND with a cold ischemic time less than 16 hours. This purpose of this criterion is to exclude subjects undergoing transplant who have very low likelihood of developing delayed graft function;

Subjects who are currently or in the past 60 days have been on experimental or as yet unapproved medications, or who have been actively enrolled in a clinical trial exploring new therapies;

Patients with a calculated panel reactive antibodies (PRA), calculated by single bead antigen of >=10%;

Graft kidneys that come from donors who are: (1) less than 30 years old, (2) who are from donors less than 40 years old with cold ischemia times <12 hours; (3) Donors whose pre-donation serum creatinine >3.0 mg/dl Pre-Transplant Assessments:

These assessments of donor, graft, and recipient (subject) factors will be included in trial database to allow stratified analyses by risk strata and/or as predictor variables in multi variable models to control for their impact on the occurrence of DGF.

Donor Factors:
  Age
  Cause of Death
  Pre-morbid conditions
  Hypertension
  Diabetes
  Weight
  Terminal Creatinine
  Donation after Cardiac Death
  Donation after Brain Death
  Expanded vs. Standard Donor Criteria
  Use of anticoagulation therapies Graft Factors:
  Warm Ischemia Time
  Cold Ischemia Time
  Machine Perfused Post vs. Cold Storage Post Harvest
  Pump parameters if machine perfused
  Preservation Solution & Buffer: UW, HTK,
  Time 0 biopsy Recipient Factors:
  Age
  Gender
  Race
  Pre-Morbid Conditions
  Diabetes
  Hypertension
  CHF
  Panel Reactive Antibodies
  Alloantibodies and Crossmatch Results
  BMI
  Duration of Dialysis Prior to Transplantation Investigational Product, Dosage:

For this Phase 2 trials, a standardized gas blend will be used which consists of 5000 parts-per-million (ppm) Carbon Monoxide in an Air matrix. The Air component is comprised of 21% Oxygen and a Nitrogen balance. The Oxygen and Nitrogen comply with the monograph requirements listed in the United States Pharmacopeia (USP) and National Formulary (NF), respectively, both of which are recognized as legal standards by the FDA.

The Carbon Monoxide ingredient is Grade 3 (99.9%), the standard grade for medical gas applications such as lung diffusion mixtures. It is blended gravimetrically with the Air matrix to a tolerance of ±5% relative (or 4750-5250 ppm). For the Phase 2 trials, the nominal mixture 5000 ppm CO will allow for dilution through the delivery device at lower concentrations (250 ppm).

Duration of Treatment:

Inhalation for approximately 1 hour (250 ppm inhaled CO or placebo) administered intraoperatively via the ventilator circuit at the onset or prior to the onset of renal graft revascularization, until the subject attains a CO-Hb level in the 8-10% target range. Similarly, on day 2 post op, subject will breath 250 ppm inhaled CO vs. placebo, for 1 hour via face mask, again targeting attained CO Hgb level of 8-10%.

Oxygen ($O_2$) 21% with balance nitrogen ($N_2$) will be used as placebo and administered as a gas for inhalation according to the same regimen as the active study drug.

Evaluation Criteria

Safety:
  Adverse events
  Discontinuations from Study
  Vital signs (temperature, blood pressure, heart rate, respiratory rate)
  Laboratory Values
  Hematology
  Serum Chemistry
  Urinalysis
  Electrocardiogram (ECG)
  $O_2$ saturation by Pulse Oxymetry
  COHbg from venous blood samples
  Neurocognitive testing battery Efficacy:
  Occurrence of delayed graft function (defined below) in week following transplant
  Markers of Renal Function in the week following transplant, and during 3 month follow-up
  Creatinine Clearance/estimated glomerular filtration rate (GFR)
  Serum Creatinine, BUN
  Urine Output
  Dialysis
  Serum Biomarkers Pharmacokinetics:

The concentration profiles of COHbg in blood will be evaluated for each subject. The PK parameters of COHb will be assessed for area under the blood concentration versus time curve (AUC0-t and AUCinf), the maximum blood concentration (Cmax), the time when the maximum blood concentration is achieved (Tmax), terminal half-life (t½), and apparent volume of distribution at steady state (Vss/F).

Delayed Graft Function Definition:

The Renal Transplant Literature has employed a number of different definitions of Delayed Graft Function (DGF). In this study, a modified dialysis-based definition will be employed. The components of this definition are as follows: (1) The necessity for dialysis in the 7 days following reperfusion of donor kidney, other than dialysis on a single occasion for the purpose of control of plasma volume or hyperkalemia rather than persistent or ongoing renal function impairment and/or (2) At 48 hours post-transplant, the failure of the estimated GFR (creatinine clearance in ml/min/m2) to improve from that observed in the first 6 hours immediately post-reperfusion of donor kidney.

Endpoints

Primary Efficacy Endpoint:

Proportion of transplant subjects satisfying DGF definition at 7 days post-transplant Secondary Efficacy Endpoints:

Trajectory of change/improvement of estimated GFR over the 7 days following reperfusion of donor kidney Trajectory of change/improvement of serum creatinine over the 7 days post-reperfusion of donor kidney Trajectory of change in estimated GFR over the first 48 hours post-reperfusion of donor kidney Creatinine reduction ratio over 2 days post-transplant: [Creat day 1]−[Creat day 2]/[Creat day 1]

Proportion of subjects with reductions in Serum Creatinine of 10%/day in each of the first 3 days after transplant GFR on Day 7 post-reperfusion of donor kidney Serum Creatinine on Day 7 post reperfusion of donor kidney Duration of Dialysis for Subjects who require it Estimated GFR at the 3 month follow-up Serum Creatinine at the 3 month follow-up Proportion of Subjects with Graft Loss/Graft Survival at the 3 month follow up Proportion of subjects with Primary Non-Function (PNF) of Graft Safety:
  Adverse Events
  SAEs (Re-hospitalization, prolongation of hospitalization, life threatening events
  Respiratory AEs, especially in during post-transplant week in hospital
  Neurocognitive AEs
  Discontinuations
  Safety Laboratory Abnormalities Allowed Medications:

All medications that are typically or routinely used in the care of patients undergoing renal transplant will be allowed in this trial. Therapies that are routinely started in the immediate post-operative period, including calcineurin inhibitors (CNIs) such as Tacrolimus and Cyclosporine, will also be allowed. Their use and doses will be recorded and included in the database to permit their use as predictor or stratifying variables in the analysis of DGF.

The mTOR inhibitors sirolimus and everolimus are excluded. Subjects who are treated with these therapies will be excluded from a 'Per Protocol' analysis, as will patients for which therapy permitted CNI inhibitors are initiated sooner than 48 hours after kidney graft reperfusion.

Data Analysis and Statistical Methods:

Adverse events will be coded using MedDRA (most current version) and summarized by treatment (Inhaled CO vs. PBO) for the number of adverse events. A by-subject treatment emergent adverse event listing including the verbatim term, preferred term, treatment, severity, and relationship to treatment will be provided. Treatment-emergent adverse events will be defined as those occurring from the time of intraoperative CO administration until 7 days post-transplant. The number of subjects experiencing adverse events and the number of adverse events will be summarized by treatment using frequency and counts. Concomitant medications will be coded using the WHO Drug Dictionary (most current version).

Safety data including renal function parameters and clinical laboratory evaluations, vital signs, electrocardiograms, and oxygen saturation assessments will be summarized by treatment and time point of collection. Descriptive statistics will be calculated for quantitative safety data and frequency and counts will be compiled for classification of the qualitative safety data. In addition, a mean change from baseline table will be provided for vital signs, pulmonary function tests, electrocardiograms, and oxygen saturation and a shift table describing out of range shifts will be provided for clinical laboratory results. Safety ECGs will be classified as normal or abnormal and summarized using frequency counts by treatment and time point of collection. The occurrence of any change in rhythm from that observed at pre-study or predose baseline will be noted. Similarly, changes in physical examination will be described in the text of the final reports.

Efficacy Outcomes:

For ordinal and categorical outcomes, descriptive statistics will be presented, with contingency table methods and comparison of frequency rates calculated. Differences in rates or frequencies by treatment group will be calculated, along with 95% confidence intervals (95% CI) for differences. Differences in means and CI of mean differences will be similarly calculated for continuous variables. In the comparison of treatment related differences for the trajectory of change of renal function variables, repeated measures analyses will be employed.

For the dichotomous primary efficacy outcome of DGF, a potential impact of the multiple donor, recipient, and graft variables/characteristics will be explored by multivariable logistic regression analysis. I Treatment will be included in all models as a dichotomous variable. In constructing a final predictor model, individual variables will be included if they add to model prediction at significant of p=0.10 or greater.

Power:

It is estimated from prior renal transplant literature that the frequency of DGF, as defined above, observed in placebo-treated subjects will be 30%. It is further hypothesized that inhaled CO Rx will be judged to have a clinically meaningful impact if it reduces the observed cumulative frequency of observed DGF to 20% in treated individuals, an absolute decline of 10%, and a relative decline of 33%.

The invention claimed is:

1. A method for improving organ or tissue function or organ or tissue transplant longevity, comprising: administering by inhaling carbon monoxide (CO)-containing gas a plurality of times to a patient in need of therapy, at a constant alveolar concentration for at least about 30 minutes;
   wherein the patient receives CO therapy a plurality of times during a perioperative period, and
   wherein the CO administration comprises at least two concentration levels of CO gas; a high level of CO to quickly reach a target CO level, and a maintenance level of CO to maintain the CO level for a period of time.

2. The method of claim 1, wherein the patient is a transplant recipient, optionally selected from kidney, liver, lung, pancreas, heart, bone marrow, and intestine.

3. The method of claim 1, wherein the patient has a condition selected from a chronic kidney fibrosing condition, a chronic hepatic fibrosing condition, a chronic lung fibrosing conditions, myocardial fibrosis, pancreatic fibrosis, pancreatitis, gastrointestinal fibrosis or strictures, vascular fibrosis or strictures, progressive systemic sclerosis (PSS), scleroderma, esophageal fibrosis or strictures, cirrhosis, atrial fibrosis, Crohn's Disease, Inflammatory Bowel Disease, paralytic ileus, arthritis, arthrofibrosis, and nephrogenic systemic fibrosis.

4. The method of claim 1, wherein the patient has pulmonary fibrosis, asthma, emphysema, Chronic Obstructive Pulmonary Disease (COPD), pulmonary arterial hypertension (PAH), cystic fibrosis (CF), Acute Respiratory Distress Syndrome (ARDS), bronchiectasis, or Ventilator-Assisted Pneumonia (VA).

5. The method of claim 2, wherein the patient is a kidney transplant recipient.

6. The method of claim 5, wherein the kidney donor is an expanded criteria donor.

7. The method of claim 1, wherein the patient receives inhaled CO therapy substantially before and/or substantially after the perioperative period.

8. The method of claim 2, wherein the patient receives the inhaled CO therapy intraoperatively.

9. The method of claim 1, wherein the patient receives CO therapy at from about 0.5 to about 5 hours prior to surgery.

10. The method of claim 1, wherein the patient receives postoperative CO therapy.

11. The method of claim 10, wherein the patient receives inhaled CO from 1 to 3 times within the first 24 hours after transplantation.

12. The method of claim 1, wherein the patient receives inhaled CO from 2 to about 10 times during the perioperative period.

13. The method of claim 12, wherein the patient receives the first two administrations of inhaled CO separated by at least about 6 hours, the first at the time of transplantation.

14. The method of claim 1, wherein the patient receives intermittent dosing after the perioperative period for prophylactic treatment.

15. The method of claim 1, wherein the patient receives inhaled CO therapy at least once per week.

16. The method of claim 1, wherein the constant alveolar concentration is maintained for at least 45 minutes, or for at least one hour.

17. The method of claim 1, wherein CO level in the patient is measured by carboxy-hemoglobin level.

18. The method of claim 17, wherein the constant alveolar concentration of CO maintains a CO-Hb level of from 8% to 12%.

19. The method of claim 1, wherein CO doses are calculated based on relationships defined by the CFK equation.

20. The method of claim 19, wherein DLco is calculated based on a CO-Hb measurement taken after from about 15 minutes to about 25 minutes of the first CO dose; and the DLco calculation is used to predict the dose of CO needed to hit the desired CO-Hb level within a specified period of time.

* * * * *